United States Patent [19]

Kelly

[11] 4,094,883

[45] June 13, 1978

[54] 5-IODO-6-OXO-3-(2'-ARYLMETHOXY-1'-HYDROXYETHYL)-4-HYDROXY-HEXANOIC ACID, γ-LACTONE DIALKYL ACETALS

[75] Inventor: Robert C. Kelly, Kalamazoo, Mich.

[73] Assignee: The Upjohn Company, Kalamazoo, Mich.

[21] Appl. No.: 784,177

[22] Filed: Apr. 4, 1977

Related U.S. Application Data

[62] Division of Ser. No. 676,895, Apr. 14, 1976, Pat. No. 4,032,542.

[51] Int. Cl.² ............................................. C07D 307/32
[52] U.S. Cl. .................................................. 260/343.6
[58] Field of Search ....................................... 260/343.6

[56] References Cited

PUBLICATIONS

Corey et al., Chem. Abst., vol. 83, 1975.

*Primary Examiner*—Natalie Trousof
*Assistant Examiner*—Jane T. Fan
*Attorney, Agent, or Firm*—Robert A. Armitage

[57] ABSTRACT

The present specification provides novel intermediates and novel processes for the synthesis of Thromboxane $B_2$ (11a-homo-11a-oxa-PGF$_{2\alpha}$), its 15-epimer, and various carboxy derivatives thereof. In particular, there are disclosed various bicyclic tetrahydrofuran-containing lactones useful in the above processes, and corresponding acyclic lactones.

2 Claims, No Drawings

5-IODO-6-OXO-3-(2'-ARYLMETHOXY-1'-HYDROXYETHYL)-4-HYDROXY-HEXANOIC ACID, γ-LACTONE DIALKYL ACETALS

The present application is a divisional application of Ser. No. 676,895, filed Apr. 14, 1976, now issued as U.S. Pat. No. 4,032,542, on June 18, 1977.

The present invention relates to Thromboxane $B_2$ and associated intermediates and processes, for which the essential material constituting a disclosure therefor is incorporated by reference here from Ser. No. 676,890, filed Apr. 14, 1976, now issued as U.S. Pat. No. 4,020,173 on Apr. 26, 1977.

I claim:

1. A thromboxane intermediate of the formula

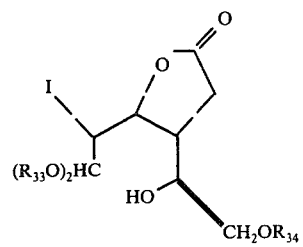

wherein $R_{34}$ is an arylmethyl hydroxy-hydrogen replacing group selected from the group consisting of
   (a) benzyl,
   (b) benzyl substituted by 1 to 5 alkyl of 1 to 4 carbon atoms, inclusive, chloro, bromo, iodo, fluoro, nitro, phenylalkyl of 7 to 12 carbon atoms, inclusive,
   (c) benzhydryl,
   (d) benzhydryl substituted by one to ten alkyl of one to four carbon atoms, inclusive, chloro, bromo, iodo, fluoro, nitro, phenylalkyl of 7 to 12 carbon atoms, inclusive,
   (e) trityl, and
   (f) trityl substituted by 1 to 15 alkyl of 1 to 4 carbon atoms, inclusive, chloro, bromo, iodo, fluoro, nitro, phenylalkyl of 7 to 12 carbon atoms, inclusive; and
wherein $R_{33}$ is alkyl of 1 to 5 carbon atoms, inclusive.

2. A thromboxane intermediate according to claim 1, wherein $R_{33}$ is methyl and $R_{34}$ is benzyl.

* * * * *